(12) United States Patent
Smith et al.

(10) Patent No.: US 6,602,226 B1
(45) Date of Patent: Aug. 5, 2003

(54) LOW-PROFILE STENT DELIVERY SYSTEM AND APPARATUS

(75) Inventors: Scott R. Smith, Chaska, MN (US); Brian J. Brown, Hanover, MN (US); David J. Blaeser, Champlin, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/689,143

(22) Filed: Oct. 12, 2000

(51) Int. Cl.[7] .............. A61M 31/00; A61M 37/00; A61M 29/00; A61F 11/00; A61F 2/06
(52) U.S. Cl. .............. 604/103.05; 606/108; 623/1.11; 604/101.02
(58) Field of Search .................. 623/1.11, 1.12; 604/104, 11, 523, 103.05, 103, 69.01, 101.05, 96.01, 96, 101, 915; 606/198, 191, 108, 192, 200

(56) References Cited

U.S. PATENT DOCUMENTS

| 5,053,008 A | 10/1991 | Bajaj | 604/104 |
|---|---|---|---|
| 5,226,889 A | 7/1993 | Sheiban | 604/101 |
| 5,320,605 A | 6/1994 | Sahota | 604/101 |
| 5,360,401 A * | 11/1994 | Turnland et al. | 604/103.05 |
| 5,409,495 A | 4/1995 | Osborn | 606/108 |
| 5,431,639 A * | 7/1995 | Shaw | 604/11 |
| 5,456,694 A | 10/1995 | Marin et al. | 606/198 |
| 5,514,093 A * | 5/1996 | Ellis et al. | 604/103 |
| 5,522,883 A | 6/1996 | Slater et al. | 623/1 |
| 5,534,007 A * | 7/1996 | St. Germain et al. | 606/191 |
| 5,571,086 A * | 11/1996 | Kaplan et al. | 604/96.01 |
| 5,578,009 A * | 11/1996 | Kraus et al. | 604/523 |
| 5,628,755 A | 5/1997 | Heller et al. | 606/108 |
| 5,632,760 A * | 5/1997 | Sheiban et al. | 604/96.01 |
| 5,634,901 A | 6/1997 | Alba et al. | 604/96 |
| 5,634,928 A | 6/1997 | Fischell et al. | 606/108 |
| 5,639,274 A | 6/1997 | Fischell et al. | 604/96 |
| 5,676,654 A | 10/1997 | Ellis et al. | 604/103 |
| 5,697,948 A | 12/1997 | Marin et al. | 606/198 |
| 5,725,535 A | 3/1998 | Hegde et al. | 606/108 |
| 5,733,299 A * | 3/1998 | Sheiban et al. | 604/101.05 |
| 5,743,874 A | 4/1998 | Fischell et al. | 604/96 |
| 5,755,708 A * | 5/1998 | Segal | 604/104 |
| 5,772,669 A | 6/1998 | Vrba | 606/108 |
| 5,788,708 A | 8/1998 | Hegde et al. | 606/108 |
| 5,807,398 A | 9/1998 | Shaknavich | 606/108 |
| 5,810,871 A | 9/1998 | Tuckey et al. | 606/198 |
| 5,951,569 A * | 9/1999 | Tuckey et al. | 606/108 |
| 5,957,930 A * | 9/1999 | Vrba | 623/1.11 |
| 6,059,813 A * | 5/2000 | Vrba et al. | 606/198 |
| 6,156,005 A * | 12/2000 | Theron | 604/101.05 |

FOREIGN PATENT DOCUMENTS

WO         96/36298         11/1996

OTHER PUBLICATIONS

U.S. patent application Ser. No. 09/032,620, Mertens, filed Feb. 1998.

* cited by examiner

Primary Examiner—Michael J. Hayes
Assistant Examiner—Roz Ghafoorian
(74) Attorney, Agent, or Firm—Vidas, Arrett & Steinkraus (57) ABSTRACT

A medical device delivery apparatus has an inner tube with a medical device receiving region at the distal end, a balloon assembly movably disposed about the inner tube and a medical balloon displaceable from the medical device receiving region. A retractable outer sheath is diposed about the inner tube and is movable relative to the inner tube to expose the medical device receiving region. An inflation lumen capable of fluid communication with the medical balloon extends proximally from the balloon. Disposed about the distal portion of the inner tube is an expandable medical device that is distal to the medical balloon. The balloon may be moved within the medical device to expand the medical device.

14 Claims, 13 Drawing Sheets

LOW-PROFILE STENT DELIVERY SYSTEM AND APPARATUS

BACKGROUND OF THE INVENTION

Delivery systems for expandable and other implantable medical devices such as stents, grafts, stent-grafts and vena cava filters are a highly developed and well known field of medical technology. Implants such as stents have many well known uses and applications. A stent is a prosthesis which is generally tubular and which is expanded radially in a vessel or lumen to maintain the patency of the vessel or lumen. Stents are widely used in body vessels, body canals, ducts or other body lumens.

The delivery systems for stents and similar medical devices are generally comprised of catheters with the medical device axially surrounding the distal end of the catheter. It is highly desirable to keep the profile of the catheter as small as possible in order to more readily pass through tortuous vessels. To that end, self-expanding and balloon expandable medical devices are ideally confined in a reduced radius for delivery to the deployment site. Once the medical device is deployed, the catheter is removed leaving the medical device implanted at the desired location in order to keep the vessel walls from closing.

Typically, separate catheters have been used to dilate a vessel and to deliver a medical device such as a stent. This requires one or more catheter exchanges during the procedure, which increases the time and cost for delivering the medical device. Some delivery systems have attempted to overcome these problems with limited success.

U.S. Pat. No. 5,632,760 to Sheiban et al (Sheiban) attempts to circumvent the problem of multiple catheter exchanges by including two balloons in a single catheter. The first balloon dilates the vessel and the second balloon expands the stent. While the Sheiban catheter allows the user to avoid multiple catheter exchanges, it presents a large profile in the region of the stent.

U.S. Pat. No. 5,810,871 to Tuckey et al (Tuckey) uses a balloon that longitudinally and slidingly runs through an expandable sheath with a stent mounted over the sheath. Such a configuration however has a relatively large profile as a consequence of 'stacking' the balloon, sheath, and stent upon one another.

There remains a need for reduced profile medical device delivery systems which use a single balloon.

For the purposes of this disclosure, the term medical prosthesis shall refer to stents, grafts, stent-grafts, vena cava filters and other expandable endoluminal prostheses.

All U.S. patents and patent applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

BRIEF SUMMARY OF THE INVENTION

In one embodiment, the invention is directed to a medical device delivery catheter comprising a slidable balloon which is initially displaced from the stent or other expandable medical device. The balloon may be moved underneath the stent to expand the stent or to seat an already expanded stent. Because the balloon is displaced from the stent, the medical device delivery catheter has a low-profile thereby allowing the catheter to be more easily manipulated and positioned within a vessel than prior higher profile catheters.

More particularly, in one embodiment, the invention is directed to a medical device delivery catheter comprising an inner tube having a medical device receiving region at the distal end and a balloon assembly movably disposed about the inner tube. The balloon assembly comprises a medical balloon displaced from the medical device receiving region. Additionally, the balloon assembly may comprise one or more sliding seals. A retractable outer sheath is disposed about the inner tube and is movable relative to the inner tube to expose the medical device receiving region. The catheter further comprises a balloon assembly engagement member capable of movably engaging the outer sheath to the balloon assembly on moving the outer sheath in a predetermined direction. The catheter further comprises an inflation lumen capable of fluid communication with the medical balloon and which supplies inflation fluid to the balloon. Finally, the catheter comprises an expandable medical device such as those disclosed above disposed about a distal portion of the inner tube, distal to the medical balloon.

In another embodiment of the invention, the catheter is constructed and arranged such that once the balloon assembly and outer sheath are engaged, distal movement of the outer sheath moves the balloon assembly in a distal direction. Proximal movement of the outer sheath results in little or no movement of the balloon.

The invention contemplates several types of unidirectional balloon assembly engagement members including a strip of oriented fibers and a hook. In one embodiment of the invention, the retractable outer sheath may be used to engage and move the balloon. In another embodiment of the invention, a push member is used to engage and move the balloon.

The invention is also directed to a method of delivering a medical device to a desired bodily location. In accordance with the method, a medical device delivery catheter is provided. The catheter has an inner tube having a medical device receiving region at the distal end and a balloon moveably disposed about the inner tube. The balloon is displaced from the medical device receiving region. The catheter further comprises a balloon moving device operably connected to the balloon and a medical device disposed about the medical device receiving region. The medical device delivery catheter is inserted into a body vessel and advanced through the vessel to a determined bodily location. The balloon is moved relative to the inner tube such that at least a portion of the balloon lies between the medical device and the inner tube and inflated thereby thereby engaging the medical device and positioning the medical device in a desired bodily location. Following positioning of the medical device, the balloon is deflated and the medical device delivery catheter withdrawn from the vessel.

Additional details and/or embodiments of the invention are discussed below.

BRIEF DESCRIPTION OF THE SEVERAL VIEWS OF THE DRAWING(S)

FIG. 3b is an enlarged view of region 3b of FIG. 3a;

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
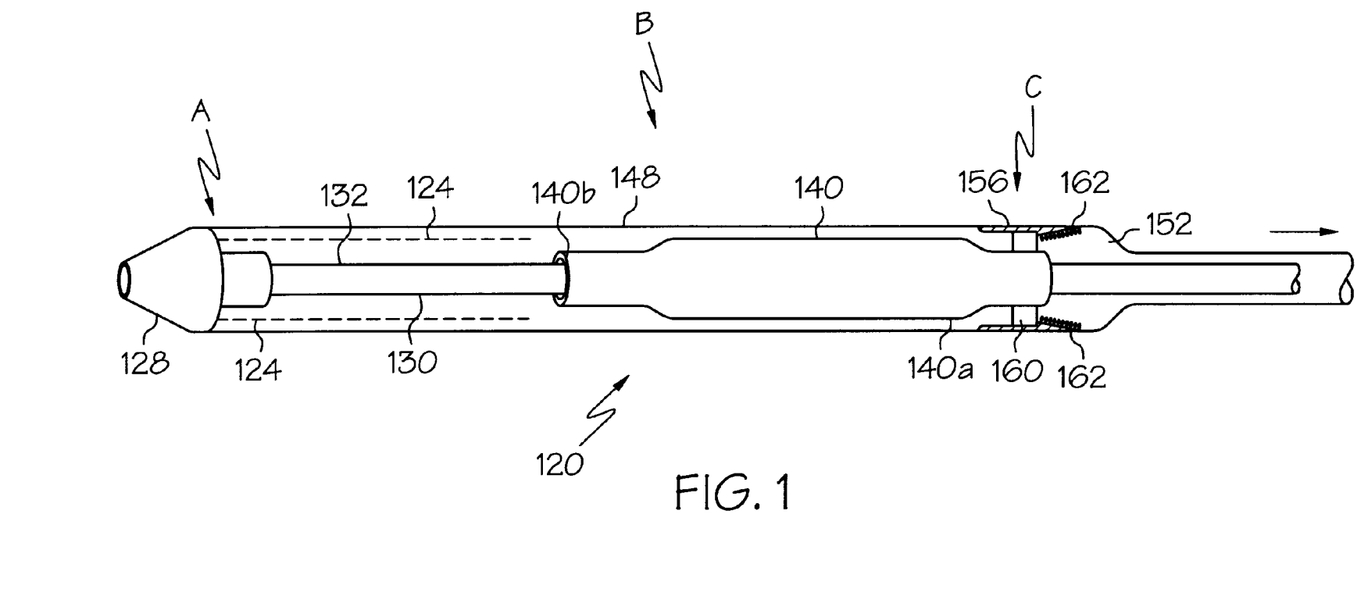
FIG. 1 is a side view with parts cut away of the distal end of an inventive medical device delivery catheter.

The present invention relates to an improved low-profile medical device deployment catheter. FIG. 1 illustrates a first embodiment of a delivery catheter 120 for deploying a medical device 124. As shown, catheter 120 has a tip 128 distally mounted upon an inner tube 132. Surrounding inner tube 132, and located proximal of the catheter tip 128 is a medical device receiving region 130 about which a medical device such as a stent 124 is disposed. Other medical devices such as grafts, stent-grafts and vena cava filters may be similarly disposed about medical device receiving region 130.

A balloon assembly comprising medical balloon 140 is disposed about inner tube 132. Medical balloon 140 is movable with respect to inner tube 132. In its initial configuration, medical balloon 140 is displaced from medical device receiving region 130. Medical balloon 140 may, however, be moved so that it underlies stent 124 and overlies medical device receiving region 130 of inner tube 132.

Medical balloon 140 is supplied with an inflation fluid via inflation lumen 152. Inflation lumen 152 is formed by the space between outer sheath 148 and inner tube 132 proximal to balloon 140. Proximal end 140a of balloon 140 is slidably sealed to outer sheath 148 via slidable seal 162 to prevent leakage of inflation fluid. Distal end 140b of balloon 140 may also be slidably sealed to inner tube 132. A slidable seal such as that disclosed in U.S. Pat. No. 5,957,930 may be suitably modified for use in the present invention. Other slidable seals, as are known in the art, may also be used. Where a slidable seal is used, the seal forms part of the balloon assembly.

Figure 2A:
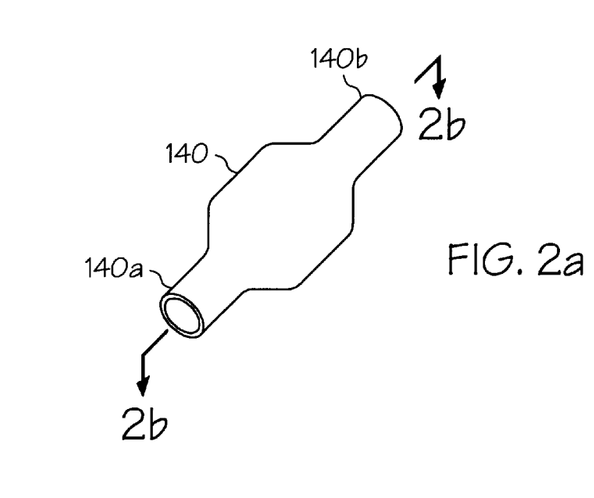
FIG. 2a shows a perspective view of a balloon which may be used in an inventive catheters.
Figure 2B:
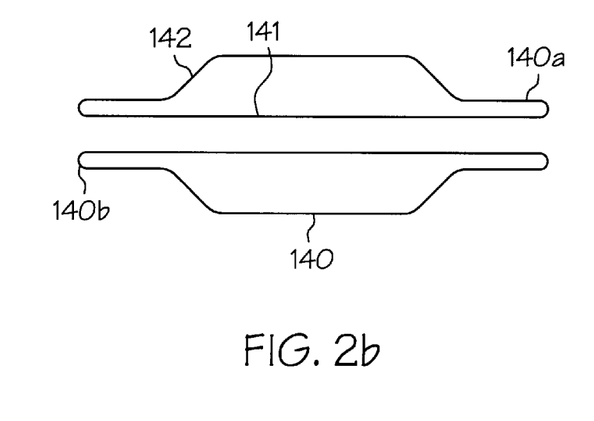
FIG. 2b shows a cross-sectional view of the balloon of FIG. 2a taken along line 2b—2b.

In lieu of slidably sealing distal end 140b of balloon 140, a double layer balloon, such as that shown at 140 in FIG. 2a may be used. As shown in transverse cross-section in FIG. 2b, balloon 140 is formed of a layer of material folded over on itself at distal end 140b of balloon 140. The balloon may be inflated by supplying an inflation fluid to the space between inner wall 141 and outer wall 142. Yet another balloon which may be used is shown in cross section at 140 in FIG. 2c. Balloon 140 contains an internal balloon member 143 which spans the interior of the balloon from proximal end 140a to distal end 140b. Balloon member 143 provides a through passage for inner tube 132. Balloon member 143 is stiff enough to prevent the balloon from collapsing in on itself along its longitudinal length as it moved relative to inner tube 132. Balloon wall 142 is sealed around both ends of balloon member 143 to form an inflatable balloon.

Figure 2C:
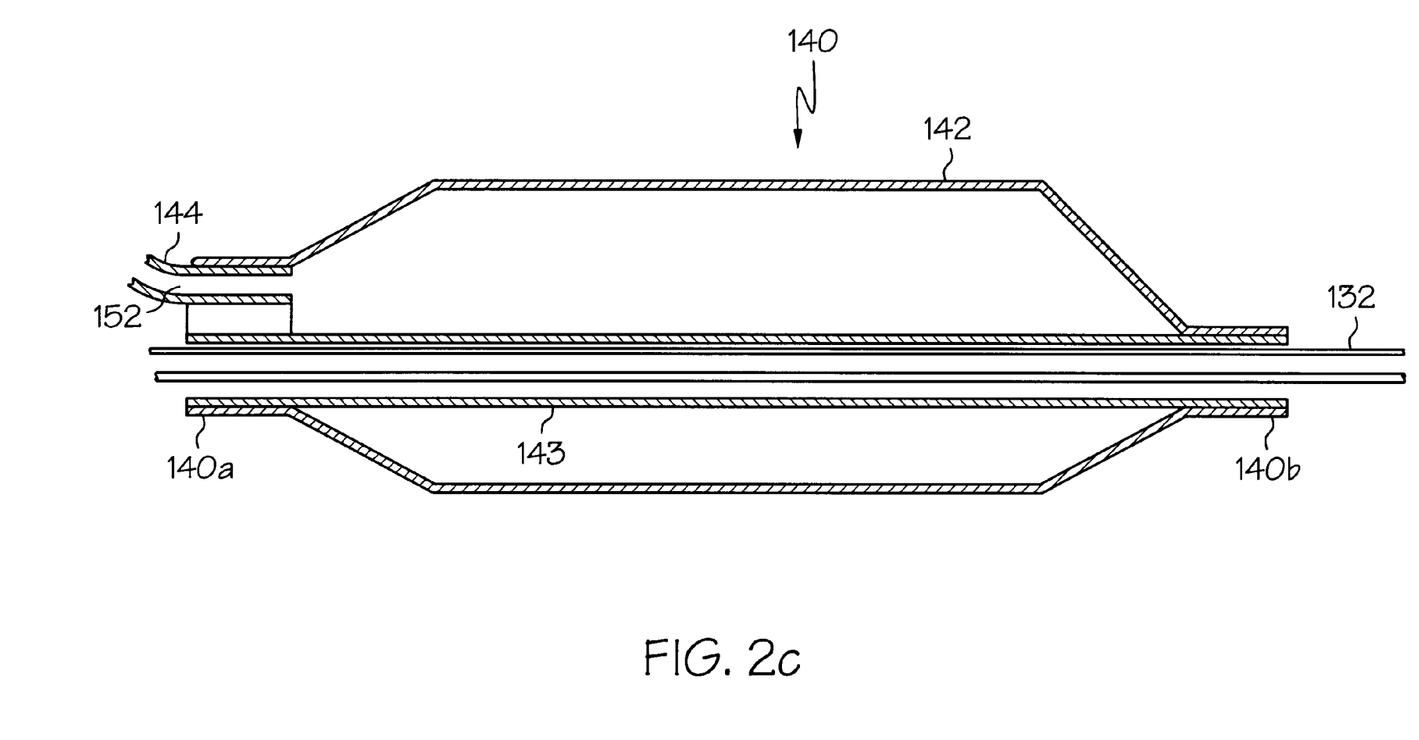
FIG. 2c shows another balloon which may be used in the inventive catheters.

Inflation tube 144 with an inflation lumen 152 therein supplies inflation fluid to the balloon. The balloon may also be supplied inflation fluid as described above in reference to FIG. 1.

Surrounding balloon 140 and stent 124 is a retractable outer sheath 148 which may be retracted beyond the proximal end of the stent for deployment of the stent. Outer sheath 148 may be a full length sheath or may extend only part of the length of the catheter. Outer sheath 148 may include a collapsible section such as that disclosed in U.S. Pat. No. 5,534,007. Outer sheath 148 may also be designed to be retractable into the catheter such as is disclosed in U.S. Pat. No. 5,772,669.

The inventive catheter 120 further comprises a unidirectional balloon assembly engagement member in the form of a strip of fibers 156 extending distally and inward from outer sheath 148 as shown in FIG. 1. Fibers 156 are constructed and arranged to engage a reciprocating member 160 which forms a part of the balloon assembly. When outer sheath 148 is moved in a proximal direction relative to balloon 140, fibers 156 slide over reciprocating member 160 and balloon 140 does not move substantially. When outer sheath is moved in a distal direction, fibers 156 engage reciprocating member 160 and move balloon 140 in a distal direction. Fibers 156 prevent balloon 140 from slipping in a proximal direction relative to outer sheath 148 unless a sufficiently large force is applied to overcome the resistance presented by oriented fibers 156.

The balloon assembly engagement member in the form of fibers 156 may be located adjacent to the proximal end 140a of balloon 140 as shown in FIG. 1 but may also be located adjacent the middle or the distal end of the balloon or in between any of these locations. Further, the balloon assembly engagement member may be located distal to the balloon at the distal end of the outer sheath. In those embodiments where the balloon assembly engagement member is located toward the distal end of the sheath, the sheath does not have to slide under the partially deployed stent in order to move the balloon into place.

Figure 3A:
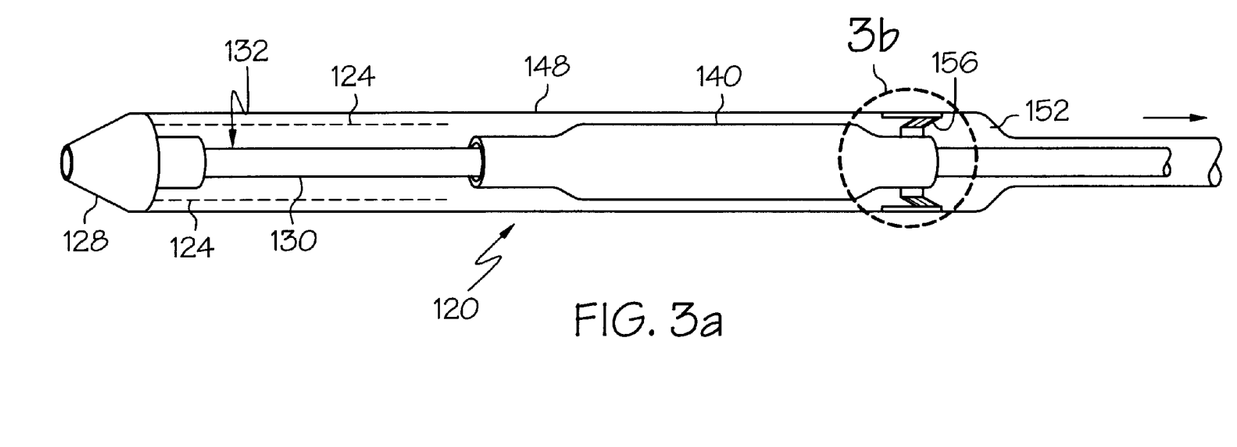
FIG. 3a is a side view with parts cut away of the distal end of an inventive medical device delivery catheter.
Figure 3B:
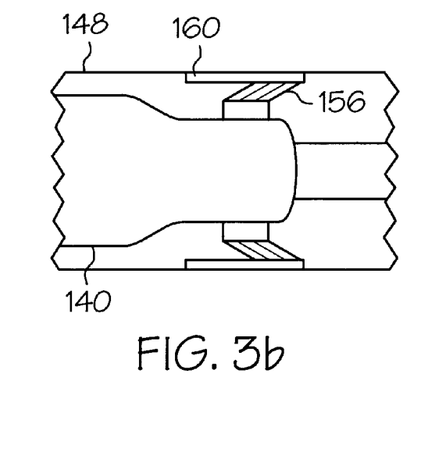

The fibers of the unidirectional balloon assembly engagement member may also be located on the balloon assembly. In that case, the reciprocating member would be disposed on the outer sheath. As shown in FIGS. 3a and 3b, fibers 156 form a part of the balloon assembly. As outer sheath 148 is moved in a proximal direction relative to balloon 140, reciprocating member 160 extending from the interior of outer sheath 148 slides over fibers 156. As outer sheath 148 is moved in a distal direction, reciprocating member 160 movably engages fibers 156 and moves balloon 140 in a distal direction thereby allowing balloon 140 to be positioned under stent 124.

Fibers 156 may be made from mohair or other natural fibers, as well as well as from synthetic fibers including polymers with a flocked or textured surface. Suitable polymers include polyethylene, polyurethane and polyimide.

The balloon assembly engagement member may also be made of an over-lapping or fishscale construction.

Figure 4A:
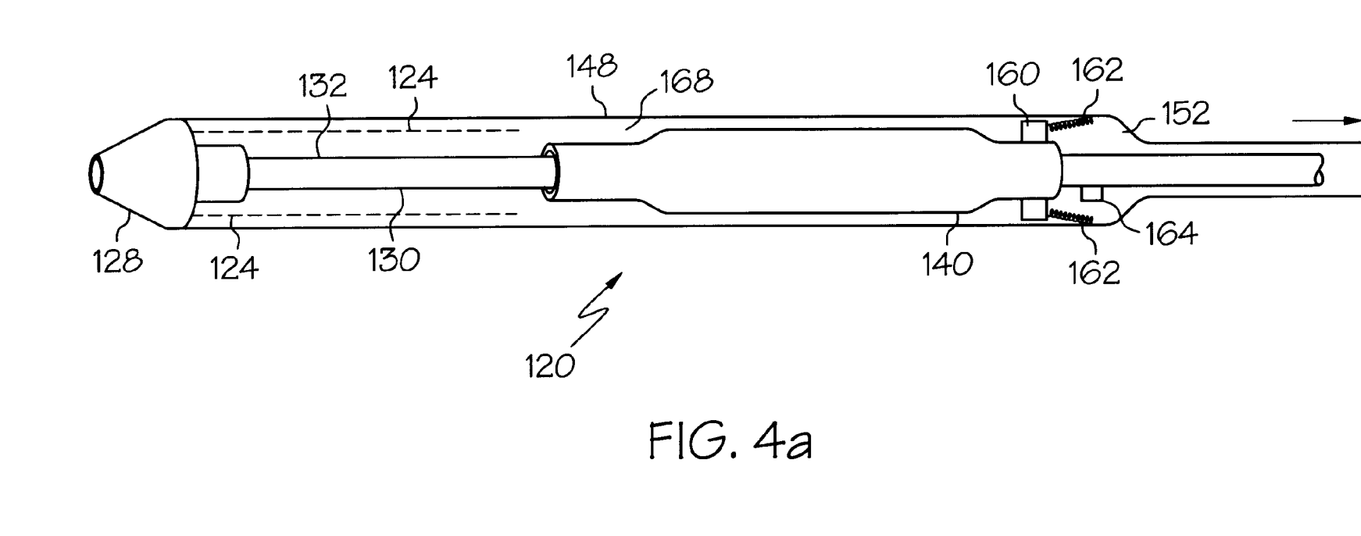
FIGS. 4a, 4b and 5–7 are side views with parts cut away of the distal end of other embodiments of the inventive medical device delivery catheter.

In another embodiment of the invention, as shown in FIG. 4a, medical device delivery catheter 120 includes a unidirectional balloon assembly engagement member in the form of a hook 168 resiliently mounted to the interior of outer sheath 148 and extending in a distal direction downward toward the inner tube from the outer sheath. A sliding seal 162 is provided to slidably seal balloon 140 and outer sheath 148. Sliding seal 162 also serves as a reciprocating member for engaging hook 168. Hook 168 is located distal of the reciprocating member prior to engagement therewith. Hook 168 is constructed and arranged to deflect toward outer sheath 148 on moving in a proximal direction over reciprocating member 160, and to return toward inner tube 130 after clearing reciprocating member. Hook 168 is further constructed to movably engage the reciprocating member when it is located proximal to the reciprocating member and being moved in a distal direction.

Figure 4B:
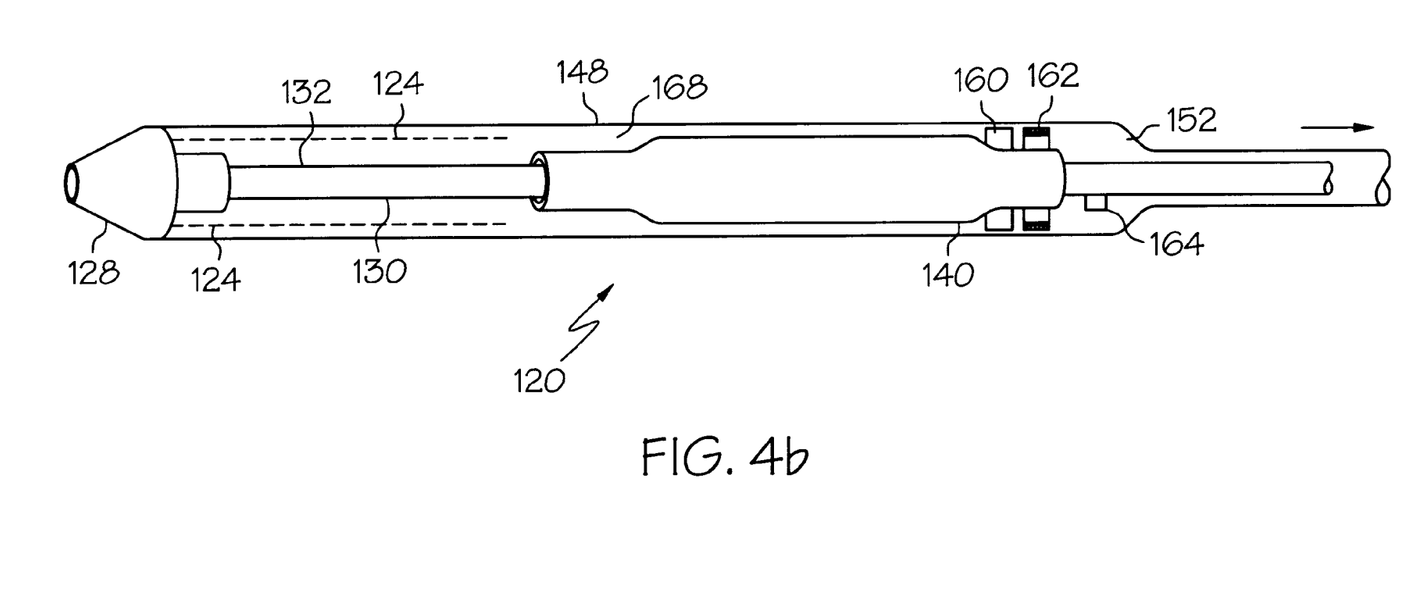

The balloon assembly may also be provided with other types of reciprocating members. As shown in FIG. 4b, a reciprocating member 160 separate from sliding seal 162 may be provided to avoid hooking on the sliding seal. Other structures as would be recognized by those of ordinary skill in the art, may also be used.

It is further noted that in the embodiment of FIG. 4a, inner tube 130 of medical device delivery catheter 120 is provided with a stop 164 proximal to the balloon assembly to prevent unwanted proximal movement of the balloon assembly. This stop may also be provided in any of the other embodiments of the invention.

Figure 5:
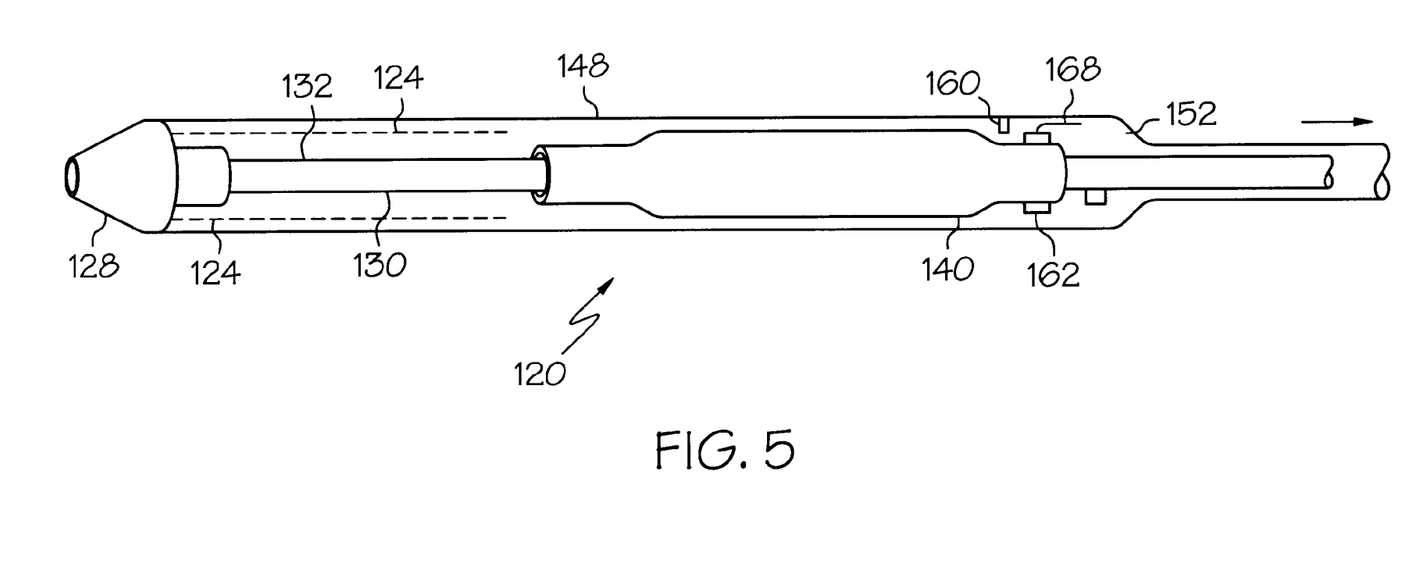

Another embodiment of the invention is shown in FIG. 5. The embodiment of FIG. 5 is similar to that of FIG. 4a with the hook mounted on the balloon assembly and the reciprocating member extending from the outer sheath. More specifically, hook 168 is resiliently mounted on the balloon assembly and extends outward from the balloon assembly toward outer sheath 148 in a proximal direction. Reciprocating member 160 extends inward from outer sheath 148 at a point distal to. hook 168, prior to engagement with hook 168. Hook 168 is constructed and arranged to deflect inward toward inner tube 130 on moving reciprocating member 160 in a proximal direction over hook 168 and to return outward toward outer sheath 148 after being cleared by reciprocating member 160. Hook 168 is further constructed to be movably engaged by reciprocating member 160 when distal to reciprocating member 160 and reciprocating member 160 is moved in a distal direction. Although not shown, the proximal end of the balloon may be slidably sealed to the outer sheath.

Figure 6:
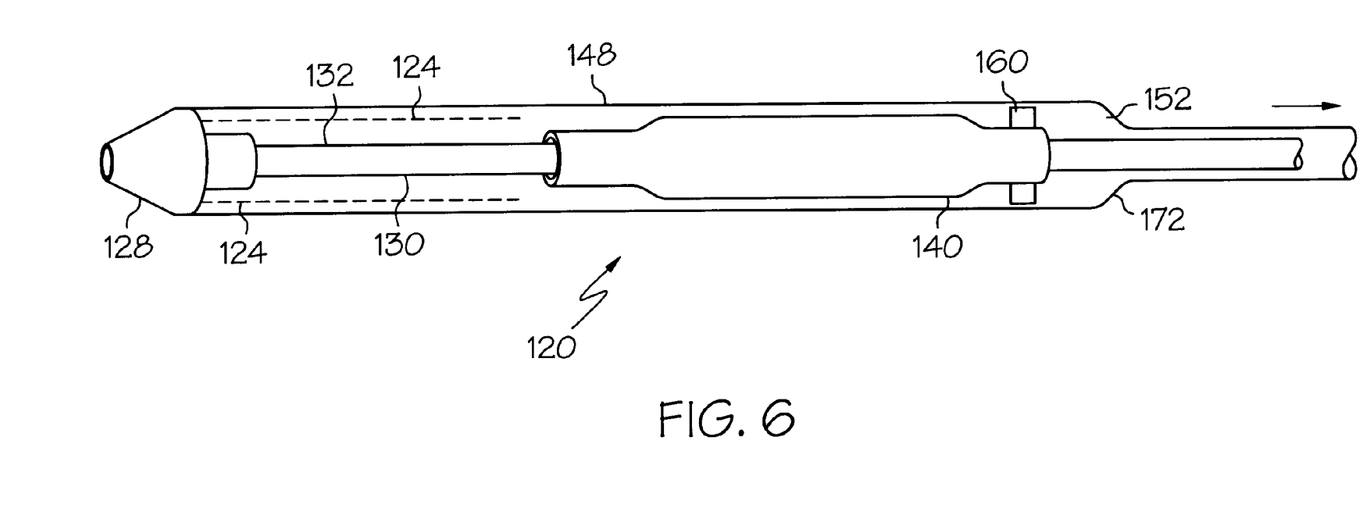

In another embodiment of the invention, as shown in FIG. 6, tip 128 has slightly smaller outer diameter than the inner diameter of outer sheath 148 so that outer sheath 148 can slide over tip 128. Outer sheath 148 has a tapered portion 172 proximal to the balloon assembly which serves as a unidirectional balloon assembly engagement member. When moved in a proximal direction, outer sheath 148 does not engage reciprocating member 160. When moved in a distal direction, tapered portion 172 of outer sheath 148 engages reciprocating member 160 which forms a portion of the balloon assembly. As the outer sheath continues to move distally, balloon 140 is moved distally into position inside of stent 124 and outer sheath 148 slides over tip 128. Outer sheath 148 is then retracted prior to inflation of balloon 140. Although not shown, the proximal end of the balloon may be slidably sealed to the outer sheath.

Figure 7:
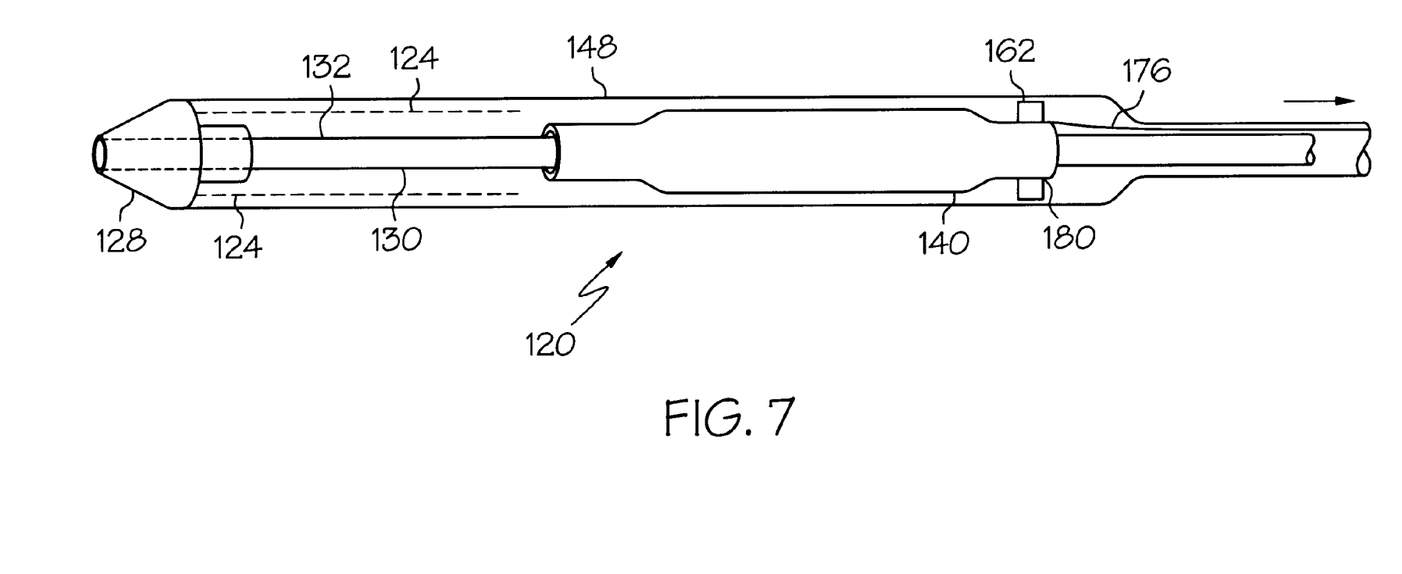

In yet another embodiment of the invention, as shown in FIG. 7, balloon 140 may be moved or held in place by rod 176 extending to the proximal end of the catheter. Rod 176 may be attached to balloon 140 by a collar 180 or by any other suitable means for attachment.

The various parts of the inventive catheter may be made of suitable materials as known by those of ordinary skill in the art.

The invention also contemplates catheters where the balloon is initially located distal to the medical device and is moved in a proximal direction to engage the medical device. The inventive catheters disclosed herein may be easily modified to achieve that end.

In use, at least the distal end of catheter 120 is inserted in a bodily vessel and advanced to a desired bodily location such as a lesion site. Once the catheter is suitably positioned at the lesion site, outer sheath 148 may be retracted thus freeing stent 124 to expand. In an embodiment utilizing a self-expanding stent, upon retraction of outer sheath 148, stent 124 will expand away from inner tube 132. Balloon 140 is then moved under stent 124, whether in the expanded or unexpanded state, and inflated. Balloon 140 may be moved using any of the balloon moving techniques associated with the above embodiments of the invention. The balloon may be moved by being frictionally or otherwise engaged by the outer sheath. The balloon may be also be moved by a pusher rod. Regardless of how the balloon is moved, balloon 140 is then inflated in order to ensure that stent 124 has been properly expanded and set into its final location within the vessel. Once stent 124 is properly set into position, balloon 140 is deflated and the entire catheter 120 is withdrawn from the vessel.

The invention is also directed to a method of delivering a medical device to a desired bodily location. In accordance with the invention, a medical device delivery catheter having an inner tube with a medical device received about the distal end and a movable balloon disposed about the inner tube and displaced from the medical device is provided. A balloon moving device is operably connected to the balloon, so that the balloon may be moveably disposed about the inner tube. The balloon moving device may be a pusher rod or a unidirectional linkage between a retractable outer sheath and the balloon. At least a portion of the medical device delivery catheter is inserted into a body vessel and advanced through the vessel to a desired bodily location. The balloon is then moved relative to the inner tube such that at least a portion of the balloon lies between the medical device and the inner tube. Whether the balloon is moved distally or proximally depends on whether the balloon is initially located proximal to the medical device or distal to the medical device. An inflation fluid is supplied to the balloon to inflate the balloon and thereby engage the medical device and position the medical device in a desired bodily location. Where the catheter includes a retractable outer sheath, the outer sheath must be retracted to expose the medical device prior to inflation of the medical balloon. The balloon is then at least partially deflated and the medical device delivery catheter withdrawn from the vessel. The outer sheath may optionally be closed subsequent to deployment of the medical device.

In another embodiment of the invention, once the catheter is properly positioned, the outer sheath is retracted from point A, as shown in FIG. 1 to point C in FIG. 1. If the stent is a self-expanding stent, the retraction of the outer sheath results in expansion of the stent. The balloon may then be advanced so that it is inside the stent and expanded to fully seat the stent. If the stent is not self expanding, the balloon may optionally be used to first dilate a lesion. The catheter is then repositioned so that the stent is properly positioned and the balloon is moved under the stent. The balloon may then be expanded to expand the stent.

Figure 8:
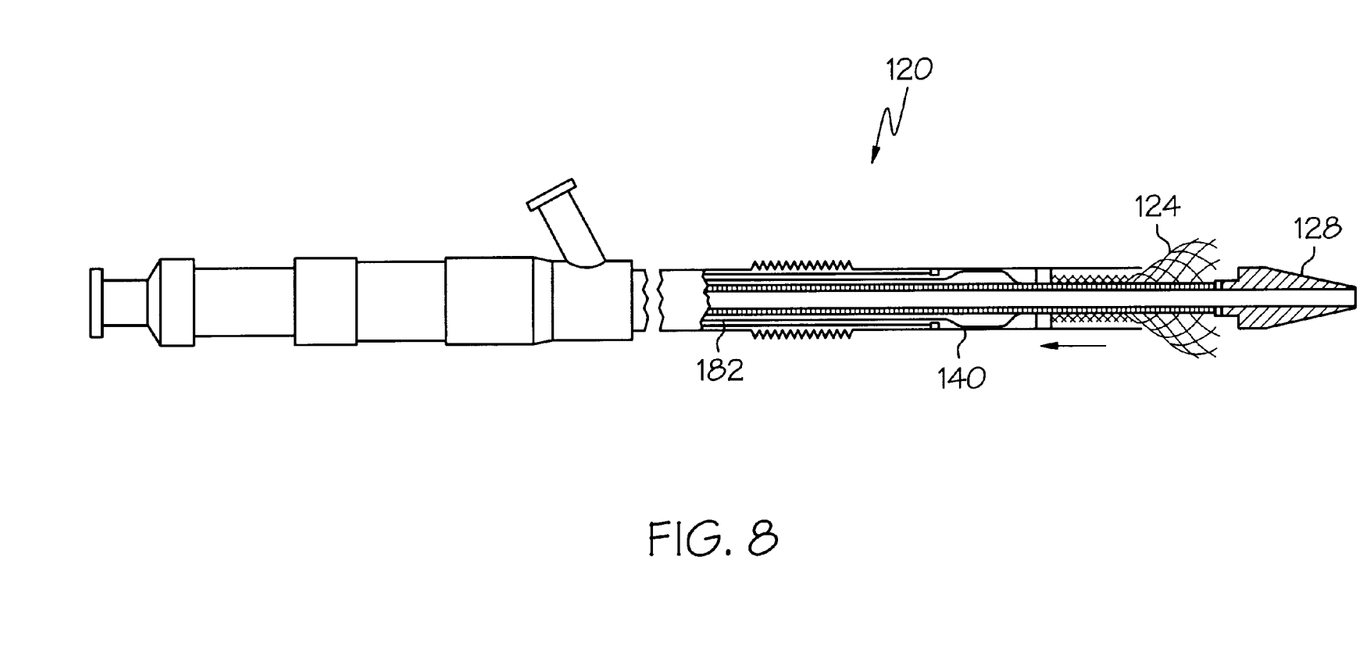
FIG. 8 is a side view with parts cut away of an inventive medical device delivery catheter.

In another embodiment of the inventive method, the outer sheath and the inner tube are both retracted, with the outer sheath leading the tip by approximately 5 mm. This approximately 5 mm lead, where a self-expanding stent is used, allows the stent to expand sufficiently for tip 128 to be withdrawn through the expanded stent, as illustrated in FIG. 8. Stent 124 has partially self-expanded. In the embodiment shown in FIG. 8, balloon 140 may be displaced using pusher rod 182.

Figure 9:
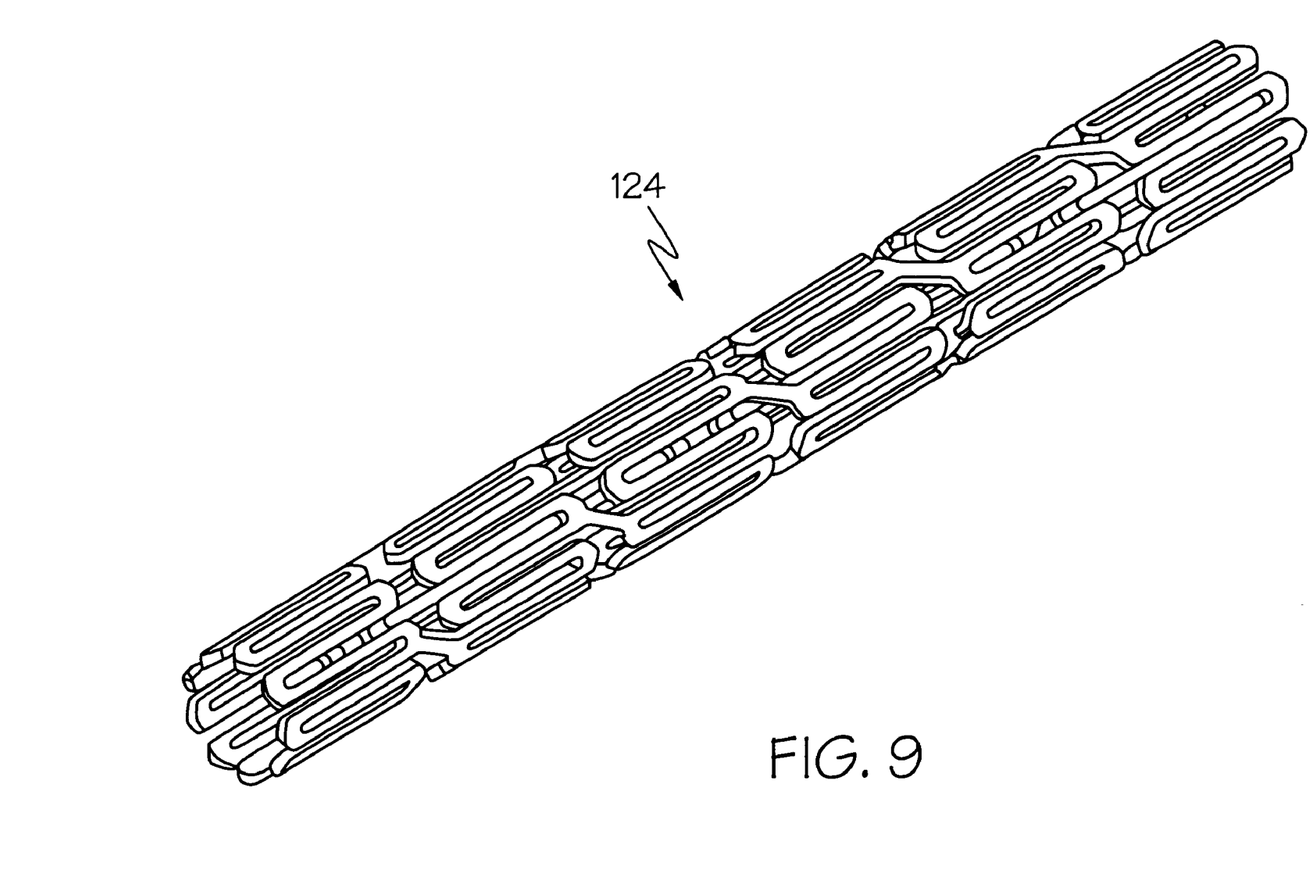
FIGS. 9–11 depict a stent, stent-graft and vena cava filter, respectively.
Figure 10:
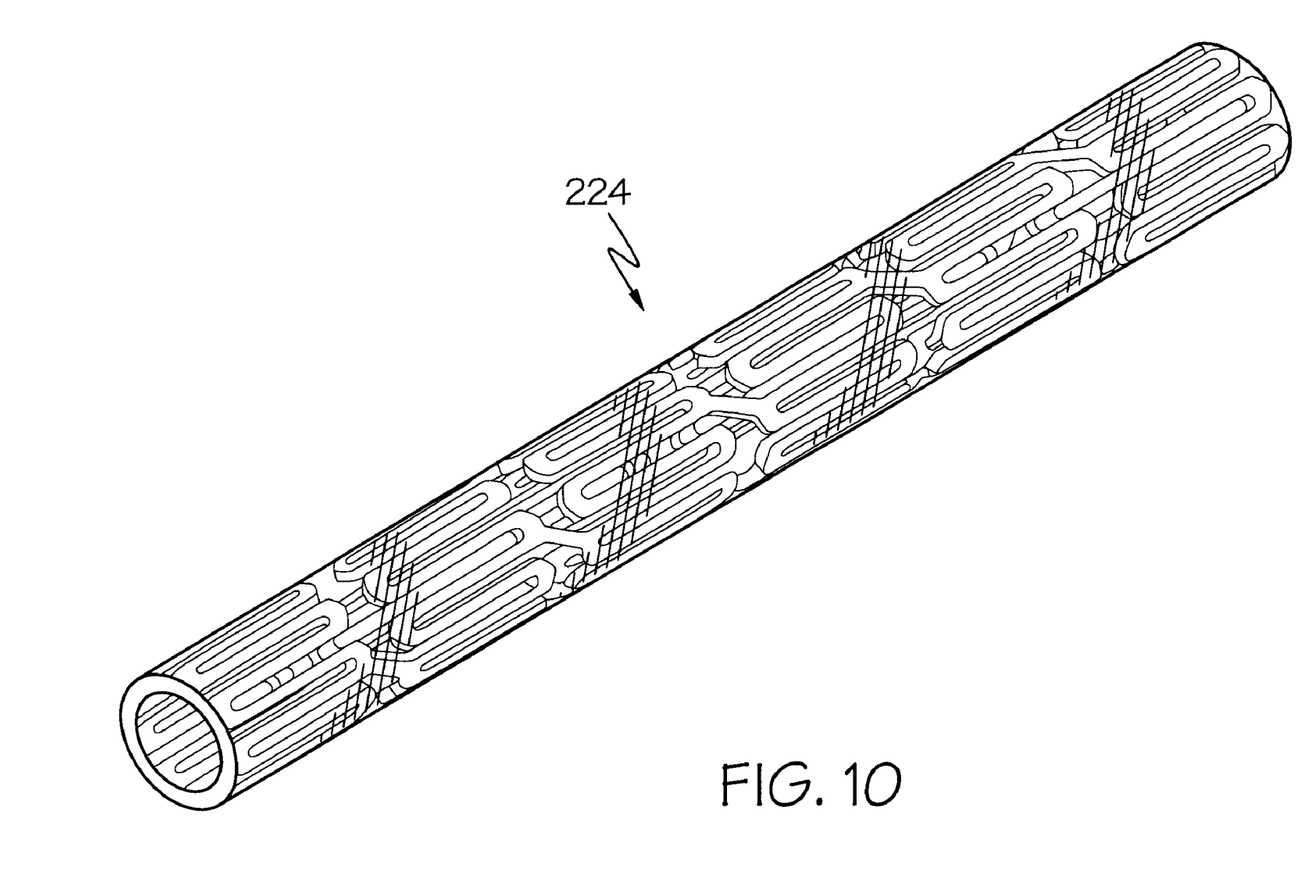
Figure 11:
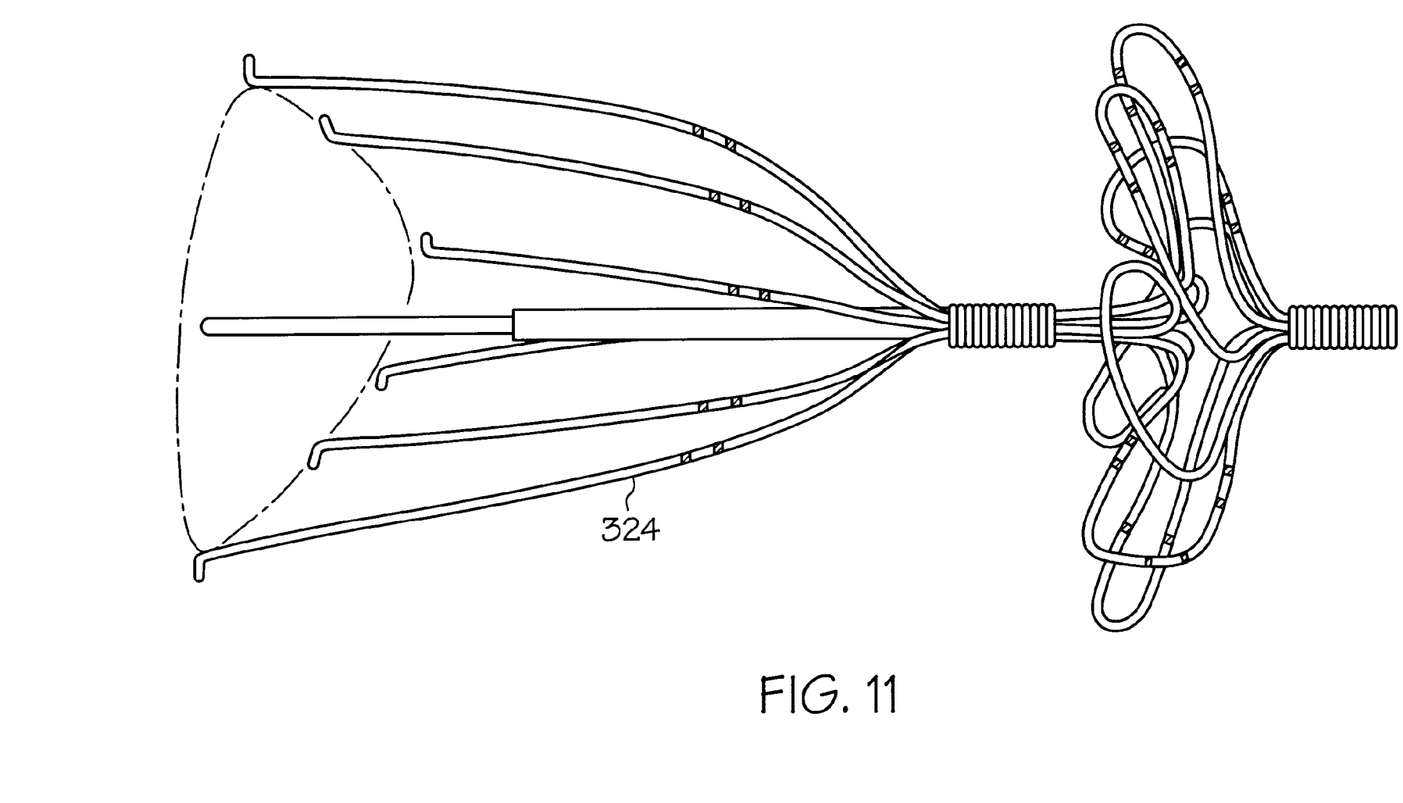

As discussed above, the medical device delivery system disclosed herein may be used to deliver a variety of medical devices including medical prostheses such as stents as shown at 124 in FIG. 9, grafts, stent-grafts as shown at 224 in FIG. 10 and vena cava filters as shown at 324 in FIG. 11 and other expandable endoluminal prostheses.

The inventive medical device delivery catheters of the present invention may be configured as rapid exchange catheters, over-the-wire catheters, fixed wire catheters or as hybrids of the above catheters.

In addition to being directed to the embodiments described above and claimed below, the present invention is further directed to embodiments having different combinations of the dependent features described above and/or claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device delivery catheter having a proximal end and a distal end comprising:
    a) an inner tube having a medical device receiving region at the distal end;
    b) a balloon assembly movably disposed about the inner tube, the balloon assembly comprising a medical balloon longitudinally displaceable from the medical device receiving region;
    c) a retractable outer sheath disposed about the inner tube and movable relative to the inner tube to expose the medical device receiving region;
    d) a balloon assembly engagement member capable of movably engaging the outer sheath to the balloon assembly only on moving the outer sheath in a distal direction relative to the inner tube, distal movement of the outer sheath moving the balloon assembly in a distal direction on being so engaged;
    e) an inflation lumen capable of fluid communication with the medical balloon and extending proximally from the balloon; and
    f) an expandable medical device disposed about the medical device receiving region.

2. The medical device delivery catheter of claim 1 wherein the inner tube has a stop thereon proximal to the balloon assembly to prevent unwanted proximal movement of the balloon assembly.

3. The medical device delivery catheter of claim 1 wherein
    the balloon assembly includes a reciprocating member for engagement by the balloon assembly engagement member,
    the balloon assembly engagement member is a hook resiliently mounted to the interior of the outer sheath and extending downward from the outer sheath in a distal direction, the hook located distal of the reciprocating member prior to engagement thereof,
    the hook constructed and arranged to deflect upward on moving in a proximal direction over the reciprocating member and to return to a downward position after clearing the reciprocating member,
    the hook further constructed to movably engage the reciprocating member when proximal to the reciprocating member and being moved in a distal direction.

4. The medical device delivery catheter of claim 3 wherein the balloon assembly further comprises a slidable seal for slidably sealing the proximal end of the balloon to the outer sheath, the slidable seal serving as the reciprocating member.

5. The medical device delivery catheter of claim 1 wherein
    the outer sheath includes a reciprocating member for engagement by the balloon assembly engagement member,
    the balloon assembly engagement member is a hook resiliently mounted to the balloon assembly and extending outward from the balloon assembly in a proximal direction, the hook located proximal of the reciprocating member prior to engagement thereof,
    the hook constructed and arranged to deflect downward on moving the reciprocating member in a proximal direction over the hook and to return to an upward position after being cleared by the reciprocating member,
    the hook further constructed to be movably engaged by the reciprocating when distal to the reciprocating member and the reciprocating member is moved in a distal direction.

6. The medical device delivery catheter of claim 1 wherein
    the balloon assembly includes a reciprocating member for engagement by the balloon assembly engagement member,
    the balloon assembly engagement member comprises a strip of fibers extending distally and inward from the outer sheath;
    the fibers constructed and arranged
        to engage the reciprocating member but not substantially displace the balloon assembly when the outer sheath is moved in a proximal direction relative to the inner tube, and
        to engage the reciprocating member and move the balloon assembly in a distal direction relative to the inner tube when the outer sheath is moved in a distal direction relative to the inner tube.

7. The medical device delivery catheter of claim 1 wherein
    the balloon assembly includes a reciprocating member for engagement by the balloon assembly engagement member,
    the balloon assembly engagement member comprises a strip of fibers extending proximally and outward from the balloon assembly, and
    the fibers constructed and arranged
        to engage the outer sheath but not substantially displace the balloon assembly when the outer sheath is moved in a proximal direction relative to the inner tube, and
        to movably engage the outer sheath such that the balloon assembly is moved in a distal direction relative to the inner tube when the outer sheath is moved in a distal direction relative to the inner tube.

8. The medical device delivery catheter of claim 1 wherein the balloon assembly engagement member is a tapered portion of the outer sheath proximal to the balloon assembly.

9. The medical device delivery catheter of claim 1 wherein the medical balloon is slidably sealed to at least one of the inner tube and the outer sheath.

10. The medical device delivery catheter of claim 1 wherein the medical device is selected from the group consisting of stents, grafts, stent-grafts and vena cava filters.

11. A medical device delivery catheter having a proximal end and a distal end comprising:
   a) an inner tube having a medical device receiving region at the distal end;
   b) a balloon assembly movably disposed about the inner tube, the balloon assembly comprising
      a medical balloon displaced from the medical device receiving region
      a reciprocating member for engagement by the balloon assembly engagement member;
   c) a retractable outer sheath disposed about the inner tube and movable relative to the inner tube to expose the medical device receiving region;
   d) a balloon assembly engagement member capable of movably engaging the outer sheath to the balloon assembly only on moving the outer sheath in a distal direction relative to the inner tube, distal movement of the outer sheath moving the balloon assembly in a distal direction on being so engaged, wherein the balloon assembly engagement member is a hook resiliently mounted to the interior of the outer sheath and extending downward from the outer sheath in a distal direction, the hook located distal of the reciprocating member prior to engagement thereof; the hook constructed and arranged to deflect upward on moving in a proximal direction over the reciprocating member and to return to a downward position after clearing the reciprocating member, the hook further constructed to movably engage the reciprocating member when proximal to the reciprocating member and being moved in a distal direction;
   e) an inflation lumen capable of fluid communication with the medical balloon and extending proximally from the balloon; and
   f) an expandable medical device disposed about a distal portion of the inner tube, distal to the medical balloon.

12. The medical device delivery catheter of claim 11 wherein the balloon assembly further comprises a slidable seal for slidably sealing the proximal end of the balloon to the outer sheath, the slidable seal serving as the reciprocating member.

13. A medical device delivery catheter having a proximal end and a distal end comprising:
   a) an inner tube having a medical device receiving region at the distal end;
   b) a balloon assembly movably disposed about the inner tube, the balloon assembly comprising
      a medical balloon displaced from the medical device receiving region;
   c) a retractable outer sheath disposed about the inner tube and movable relative to the inner tube to expose the medical device receiving region, the outer sheath includes a reciprocating member for engagement by the balloon assembly engagement member;
   d) a balloon assembly engagement member capable of movably engaging the outer sheath to the balloon assembly only on moving the outer sheath in a distal direction relative to the inner tube, distal movement of the outer sheath moving the balloon assembly in a distal direction on being so engaged, wherein the balloon assembly engagement member is a hook resiliently mounted to the balloon assembly and extending outward from the balloon assembly in a proximal direction, the hook located proximal of the reciprocating member prior to engagement thereof, the hook constructed and arranged to deflect downward on moving the reciprocating member in a proximal direction over the hook and to return to an upward position after being cleared by the reciprocating member, the hook further constructed to be movably engaged by the reciprocating when distal to the reciprocating member and the reciprocating member is moved in a distal direction;
   e) an inflation lumen capable of fluid communication with the medical balloon and extending proximally from the balloon; and
   f) an expandable medical device disposed about a distal portion of the inner tube, distal to the medical balloon.

14. A medical device delivery catheter having a proximal end and a distal end comprising:
   a) an inner tube having a medical device receiving region at the distal end;
   b) a balloon assembly movably disposed about the inner tube, the balloon assembly comprising a medical balloon longitudinally displaceable from the medical device receiving region;
   c) a retractable outer sheath disposed about the inner tube and movable relative to the inner tube to expose the medical device receiving region;
   d) a balloon assembly engagement member capable of movably engaging the outer sheath to the balloon assembly only on moving the outer sheath in a distal direction relative to the inner tube, distal movement of the outer sheath moving the balloon assembly in a distal direction on being so engaged;
   e) an inflation lumen capable of fluid communication with the medical balloon and extending proximally from the balloon; and
   f) a stent or stent graft disposed about the medical device receiving region such that the stent or the stent graft upon being crimped does not move longitudinally in relation to the inner tube before expansion.

* * * * *